(12) United States Patent
Bian et al.

(10) Patent No.: US 9,120,816 B2
(45) Date of Patent: Sep. 1, 2015

(54) OXANORBORNADIENE DERIVATIVES AND THEIR ANTICANCER ACTIVITIES

(71) Applicant: Hong Kong Baptist University, Hong Kong (HK)

(72) Inventors: Zhaoxiang Bian, Hong Kong (HK); Chengyuan Lin, Hong Kong (HK); Baomin Fan, Yunnan (CN); Huaixue Mu, Hong Kong (HK); Yongyun Zhou, Yunnan (CN); Weimin Zeng, Yunnan (CN); Aiping Lu, Hong Kong (HK); Albert Sun Chi Chan, Hong Kong (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 14 days.

(21) Appl. No.: 14/108,281

(22) Filed: Dec. 16, 2013

(65) Prior Publication Data

US 2014/0187626 A1 Jul. 3, 2014

Related U.S. Application Data

(63) Continuation-in-part of application No. 13/729,479, filed on Dec. 28, 2012.

(51) Int. Cl.
C07D 307/92 (2006.01)
C07D 493/08 (2006.01)
C07D 307/93 (2006.01)

(52) U.S. Cl.
CPC ............ *C07D 493/08* (2013.01); *C07D 307/93* (2013.01)

(58) Field of Classification Search
CPC ..................................................... C07D 307/93
USPC ......................................................... 549/459
See application file for complete search history.

(56) References Cited

PUBLICATIONS

Hu et al, Org Biomol Chem, vol. 11 pp. 2294-2301 (2013) C3OB27382B.*
Jun Hu et al., A study on the substituent effects of norbornadiene derivatives in iridium-catalyzed asymmetric [2+2] cycloaddition reactions, Organic & Biomolecular Chemistry, 2013, 11(14), p. 2294-2301.
Bao-Min Fan et al., Asymmetric hydroalkynylation of norbornadienes promoted by chiral iridium catalysts, Angew Chem Int Ed., 2012, 51(31), p. 7821-7824.
Wen-Wen Huang et al., Cantharidin induces G2/M phase arrest and apoptosis in human colorectal cancer colo 205 cells through inhibition of CDK1 activity and caspase-dependent signaling pathways, International Journal of Oncology, 2011, 38(4), p. 1067-73.
Carlos E. Puerto Galvis et al., Cantharidin-based small molecules as potential therapeutic agents, Chem Biol Drug Des, 2013, 85(5), p. 477-499.
Andriy G. Golub et al., Discovery and characterization of synthetic 4'-hydroxyflavones—New CK2 inhibitors from flavone family, Bioorganic & Medicinal Chemistry, 2013, 21(21), p. 6681-6689.

(Continued)

*Primary Examiner* — Andrew D Kosar
*Assistant Examiner* — Raymond Covington
(74) *Attorney, Agent, or Firm* — Ella Cheong Hong Kong; Sam T. Yip

(57) ABSTRACT

The present invention relates to chemical entities originated from natural sources and further synthesized for therapeutic uses. More particularly, the present invention relates to norcantharidin analogs synthesized by a transition metal-catalyzed alkynylation of oxanorbornadiene derivatives and their antitumor effects.

16 Claims, 3 Drawing Sheets

(56) References Cited

PUBLICATIONS

Dongwu Liu et al., Effect of norcantharidin on the human breast cancer Bcap-37 cells, Connective Tissue Research, 2012, 53(6), p. 508-512.

Mariangela Rondanelli et al., Health-promoting properties of artichoke in preventing cardiovascular disease by its lipidic and glycemic-reducing action, Monaldi Arch Chest Dis, 2013, 80(1), p. 17-26.

Jun Hu et al., Iridium-catalyzed asymmetric hydroalkynylation reactions of oxabenzonorbornadienes, Organic & Biomolecular Chemistry, 2013, 11(5), p. 814-820.

Bao-Min Fan et al., Ligand-controlled enantioselective [2+2] cycloaddition of oxabicyclic alkenes with terminal alkynes using chiral iridium catalysts, Organic Letters, 2010, 12(2), p. 304-306.

Chun-Chao Chang et al., Liposome encapsulation reduces cantharidin toxicity, Food and Chemical Toxicology, 2008, 46(9), p. 3116-3121.

Lesley-Ann Giddings et al, Microbial natural products: molecular blueprints for antitumor drugs, J Ind Microbiol Biotechnol., 2013, 40(11), p. 1181-1210.

You-Ming Jiang et al., Norcantharidin Induces HL-60 Cells Apoptosis in Vitro, Evidence-Based Complementary and Alternative Medicine, 2012, 2012, p. 1-4.

Ya-Chun Lee et al., Norcantharidin suppresses cell growth and migration with enhanced anticancer activity of gefitinib and cisplatin in human non-small cell lung cancer cells, Oncol Rep, 2012, 29(1), p. 237-243.

Dongwu Liu et al., The effects of cantharidin and cantharidin derivates on tumour cells, Anti-Cancer Agents in Medicinal Chemistry, 2009, 9(4), p. 392-396.

Shibata et al., Org. Let. vol. 8, No. 7 pp. 1343-1345 (2006).

\* cited by examiner

OXANORBORNADIENE DERIVATIVES AND THEIR ANTICANCER ACTIVITIES

CROSS-REFERENCE TO RELATED APPLICATIONS

The present application is a continuation-in-part application of the U.S. non-provisional patent application Ser. No. 13/729,479 filed Dec. 28, 2012, which the disclosure is hereby incorporated by reference in its entirety.

FIELD OF INVENTION

The present invention relates to chemical entities originated from natural sources or obtained from a chemically synthesized compound and further synthesized for therapeutic uses. More particularly, the present invention relates to norcantharidin analogues synthesized by a transition metal-catalyzed alkynylation of oxanorbornadiene derivatives and their antitumor effects.

BACKGROUND OF INVENTION

Natural products reflect good biological activities in many ways, particularly in the treatment of cancers, inflammation, cardiovascular disease and immune disease. Cantharidin (see Formula (a)) is a natural anti-tumor drug obtained from the dried body of the Chinese blister beetles. Its clinical application is limited due to severe side-effects and highly toxicity. Norcantharidin (see Formula (b)), a derivative of cantharidin, can reduce the side-effect in the urinary system to some extent and increase the number of white blood cells with comparable anti-cancer activity. Both of them have been used as an anti-cancer agent in clinical application, by inducing apoptosis in many types of tumor cells, such as hepatoma, breast, oesophageal, colorectal and lung carcinoma, etc. Based on these natural products, a lot of small molecule drugs were synthesized to expand the clinical application. Our target is to explore better analogues of norcantharidin with better anti-cancer activity and less side-effects.

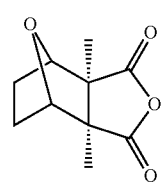

Formula (a)

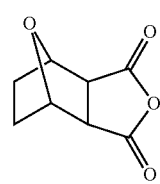

Formula (b)

Our group mainly aimed at the asymmetric reactions of norbornadiene derivatives with terminal alkynes. Recently, it was reported in Fan, B. M., et al. (*Ligand-controlled enantioselective [2+2] cycloaddition of oxabicyclic alkenes with terminal alkynes using chiral iridium catalysts*. Org Lett, 2010. 12(2): p. 304-6, and Hu, J., et al., *A study on the substituent effects of norbornadiene derivatives in iridium-catalyzed asymmetric [2+2] cycloaddition reactions*. Org Biomol Chem, 2013. 11(14): p. 2294-301) that mixture of iridium and chiral xylyl-phanephos is an efficient catalyst for the [2+2] cycloadditions of norbonadiene derivatives and terminal alkynes (up to 99% ee). Interestingly, when the diphosphine ligand by simply changing from planar chiral to axial chiral (e.g. SYNPHOS), hydroalkynylation products were generated instead by direct addition the C—H bond of terminal alkynes to the C=C bond of norbornadienes derivatives. Fan et al. also found that the hydroalkynylation products of 7-oxabenzonorbornadienes derivatives have shown good anti-cancer activities (U.S. patent application Ser. No. 13/729,479).

Citation or identification of any reference in this section or any other section of this application shall not be construed as an admission that such reference is available as prior art for the present application.

SUMMARY OF INVENTION

Accordingly, it is an object of the present invention to provide a type of norcantharidin analogues comprising the basic structure of formula (I):

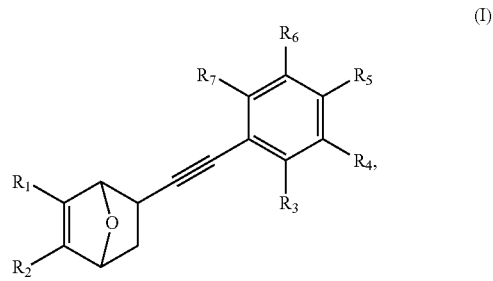

(I)

wherein $R_1$ and $R_2$ are independently or jointly selected from hydrogen, halogen, alkyl, alkenyl, alkynyl, hydroxyl, alkoxyl, amine, nitro, alkylthio, or heteroalkyl, and wherein $R_3$, $R_4$, $R_5$, $R_6$, and $R_7$ are independently or jointly selected from hydrogen, halogen, alkyl, alkenyl, alkynyl, hydroxyl, alkoxyl, amine, nitro, nitrile, alkylthio, trifluoromethyl, alkyl sulfonyl, or aryl sulfonyl. The norcantharidin analogues of the present invention are originated from natural sources and further synthesized into at least three different compounds. In one embodiment, at least three compounds namely compounds 1, 2 and 3 [or named as formulae (II), (III) and (IV), respectively, in other parts of the present application] are originated from the natural sources and further synthesized to result in one of the following structures:

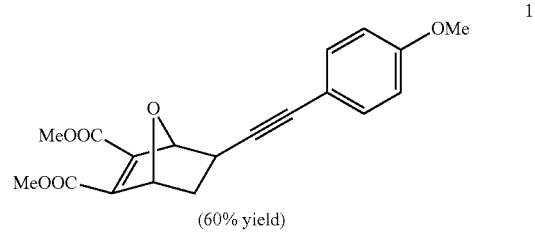

1

(60% yield)

-continued

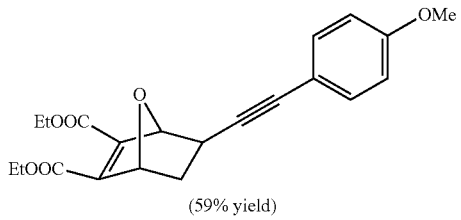

(59% yield)

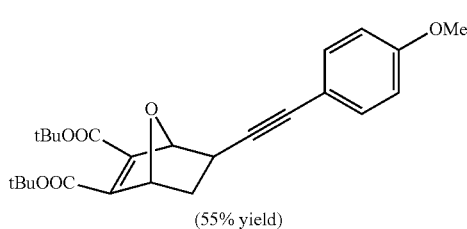

(55% yield)

In one aspect of the present invention, there is provided a method of synthesizing the compounds 1, 2 and/or 3 comprising using an Ir catalyst to carry out transition metal-catalyzed alkynylation of oxanorbornadiene derivatives originated from natural sources or obtained from a chemically synthesized compound, wherein the Ir catalyst comprises Ir(I)(COD)Cl, [Ir(I)(COD)Cl]$_2$, Ir(I)(COD)(acac) and Ir(III)($C_7H_8$)$_3$(acac).

In another aspect of the present invention, there is provided a reaction solvent used in the method of synthesizing the compounds 1, 2 and/or 3 comprising 1,2-dichloroethane (DCE), tetrahydrofuran (THF), dimethoxyethane (DME), toluene, EtOAc and i-PrOH.

In one aspect of the present invention there is provided a method of using the compounds 1, 2 and/or 3, or a composition comprising a therapeutically effective amount of compounds 1, 2 and/or 3 in treatments of cancerous tumors.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which:

FIG. 2 shows wound healing assay of compounds 1, 2 and 3 on human esophageal carcinoma (KYSE-150) cells.

DETAILED DESCRIPTION OF INVENTION

The present invention is not to be limited in scope by any of the specific embodiments described herein. The following embodiments are presented for exemplification only.

Figure 1:
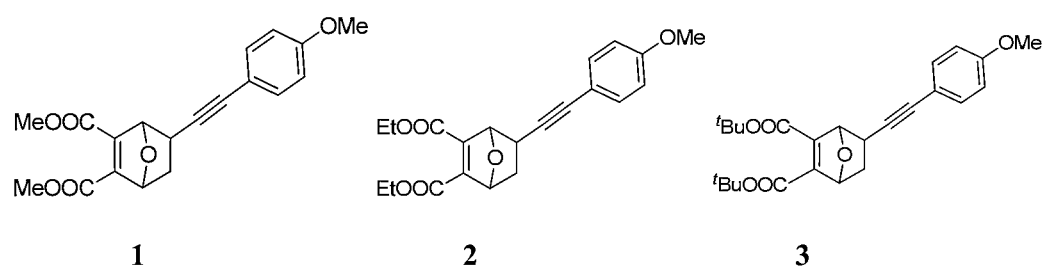
FIG. 1 shows compounds 1, 2 and 3.

In one embodiment of the present invention, three hydroalklation products (see FIG. 1, compounds 1, 2, 3) are synthesized. All compounds are evaluated for their anti-cancer activities against MDA-MB-231, MCF-7, MKN-45, KYSE-150, HepG2 and DLD-1 cell lines using the cell viability assay by the MTT method. Anti-migration activity of each of the compounds is measured by wound healing assay against KYSE-150 cell line.

Result and Discussion

Synthetic method had been optimized in Hu, J., et al. [*Iridium-catalyzed asymmetric hydroalkynylation reactions of oxabenzonorbornadienes*. Org Biomol Chem, 2013. 11(5): p. 814-20], which is hereby incorporated by reference in its entirety. In one embodiment of the present invention, three substituted oxanorbornadiene derivatives are used in the hydroalkynylation reaction with 4-Ethynylanisole afforded corresponding products in moderate yield (Scheme 1).

Scheme 1. The iridium catalyzed hydroalkylation reaction of oxanorbornadiene derivatives with 4-Ethynylanisole

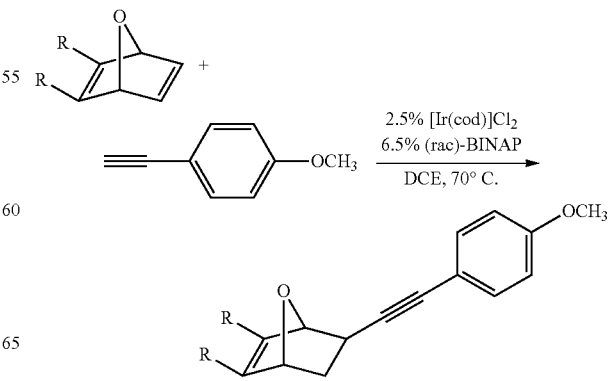

-continued

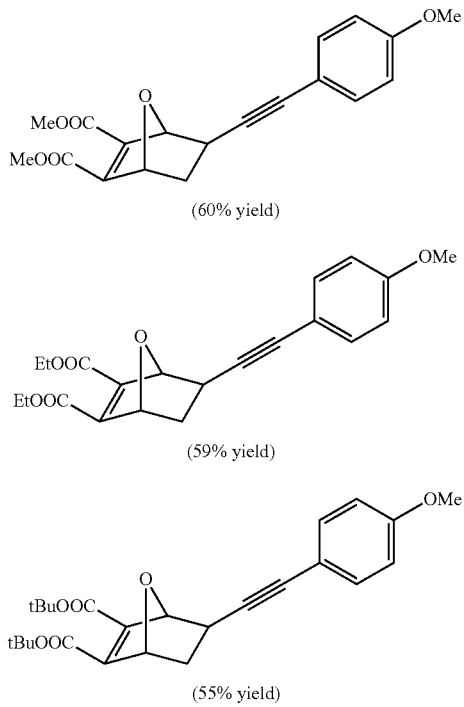

(60% yield) 1

(59% yield) 2

(55% yield) 3

Cytotoxic activities of all compounds are evaluated by MTT assay using KYSE-150 (human oesophagus carcinoma), MKN-45 (human gastric aednocarcinoma), DLD-1 (human colorectal carcinoma cell line), HepG2 (human hepatocellular carcinoma), MCF-7 (human breast adenocarcinoma), and MDA-MB-231 (human breast adenocarcinoma). Canthatidin is used as positive control. $IC_{50}$ values are shown in Table 1.

TABLE 1

Cytotoxicity of Novel Compounds against Four Cancer Cell Lines [a]

| Compound | MDA-MB-231 | MCF-7 | KYSE-150 | MKN-45 | HepG2 | DLD-1 |
|---|---|---|---|---|---|---|
| 1 | 2.30 | 2.46 | 1.82 | 21.33 | 6.20 | 6.00 |
| 2 | 2.81 | 6.39 | 1.40 | 26.00 | 15.66 | 1.74 |
| 3 | 50.20 | 33.40 | 5.40 | 6.31 | 8.40 | 3.77 |
| Canthari din[b] | 4.69 | 12.99 | 3.10 | 4.518 | 3.10 | 13.87 |

[a] Results are expressed as $IC_{50}$ values in µM.
[b] Positive control.

Figure 2A:
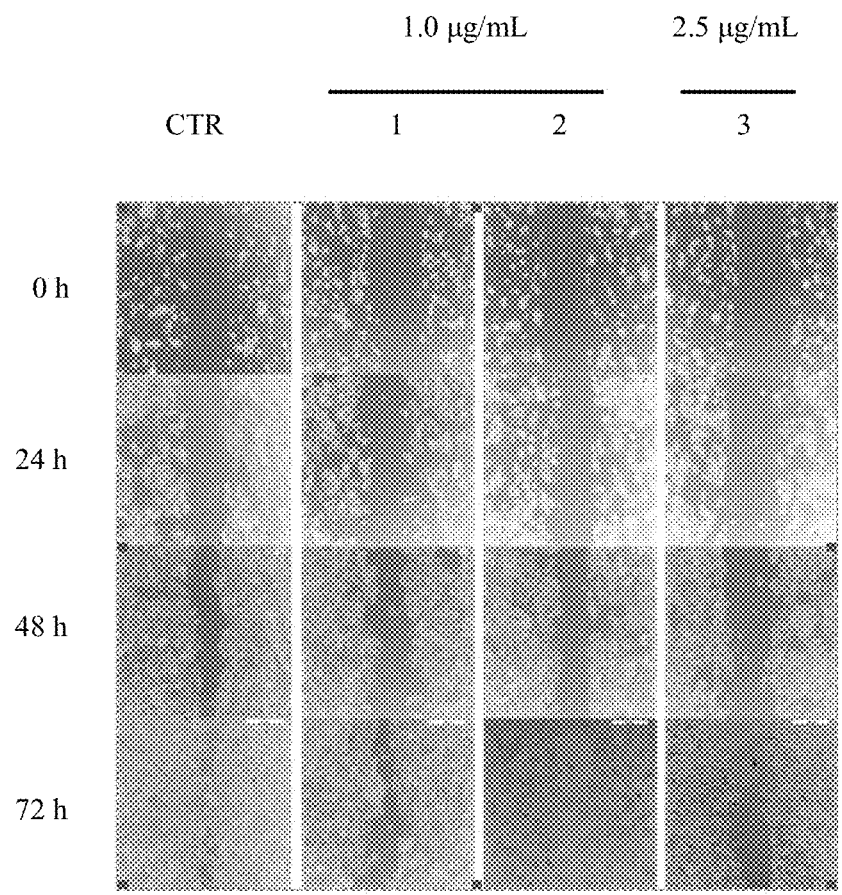
FIG. 2A: CTR is control group, 1 µg/mL compounds 1 and 2 treated group, 2.5 µg/mL compound 3 treated group.
Figure 2B:
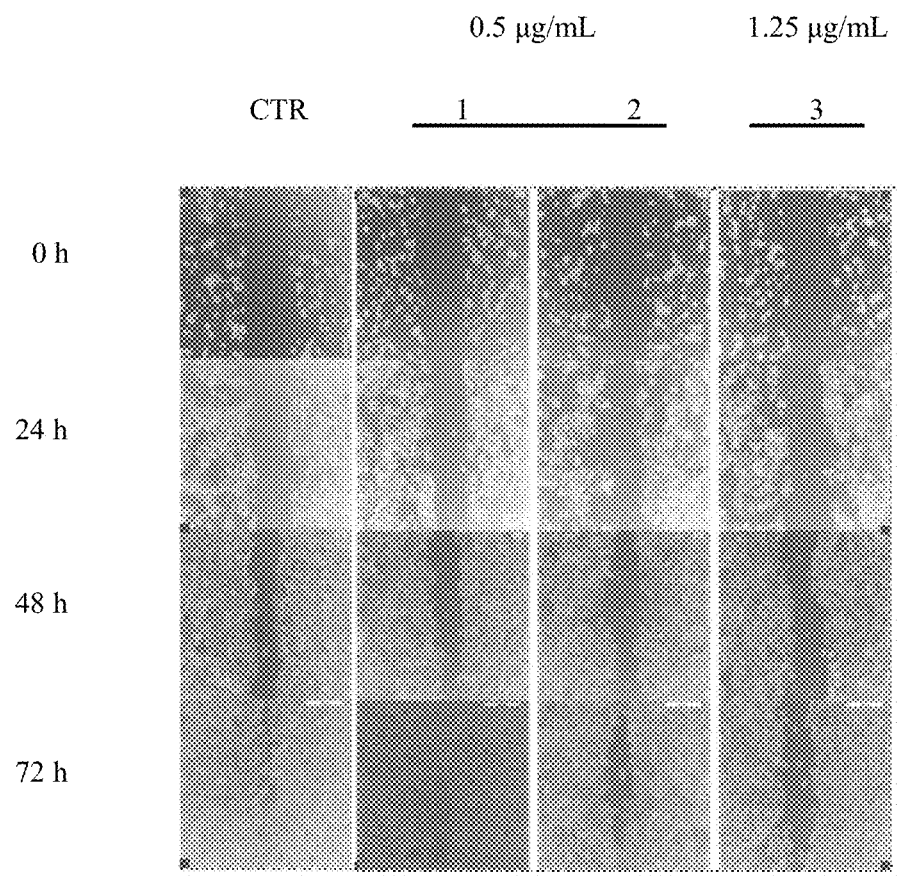
FIG. 2B: CTR is control group, 0.5 µg/mL compounds 1 and 2 treated group, 1.25 µg/mL compound 3 treated group.

In addition, wound healing assay is used to test whether the compounds 1, 2 and 3 could affect cell motility. A confluent monolayer of KYSE-150 cells is scratched to form a wound and incubated in the absence or presence of the tested compounds at the concentrations of 1 and 2.5 µM/mL (compounds tested at the highest concentration of 1 µM/mL and 2.5 µM/mL do not alter the viability of KYSE-150 cells as compared to that of controls). After 72 h, the wound edges are indistinguishable in control group, while the compounds 1, 2 and 3 (from FIG. 1) treated cells do not migrate into the wound (FIGS. 2A and 2B), indicating that they have anti-migration effect on KYSE-150 cells in the absence of cytotoxicity.

Conclusion

In short, the three compounds show significant anti-cancer and anti-migration activities. Compared with the positive control of canthatidin, compound 1 inhibits cell growth of KYSE-150, MKN-45, DLD-1, MDA-MB-231 and MCF-7 cells in terms of the $IC_{50}$ values which are below 10 µM/mL. Compound 2 also has growth-inhibiting effects on KYSE-150, MDA-MB-231 and MCF-7 cells as compared to positive control. Compound 3 has growth-inhibiting effects on DLD-1 cells as compared to positive control. From these studies, it is observed an effective amount of compound 1, 2 and 3 for anti-cancer and anti-migration can range from 1 µM/mL to 10 µM/mL.

Experimental Section

General Remarks

The reactions and manipulations are performed under an atmosphere of argon by using standard Schlek techniques and Drybox (Mikrouna, Supper 1220/750). Anhydrous 1,2-dichloroethane (DCE) is distilled from calcium hydride and stored under argon. Alkynes are purchased from Sigma-Aldrich Company, chiral ligands are purchased from Strem company, and oxanorbornadiene are synthesized according to the reported procedures in Hu et al. $^1$H NMR and $^{13}$C NMR spectra are recorded on Bruker-Avance 400 or 500 MHz spectrometer. $CDCl_3$ is used as solvent. Chemical shifts (δ) are reported in ppm with tetramethylsilane as internal standard, and J values are given in Hz. High resolution mass spectra (HRMS) are performed on a VG Autospec-3000 spectrometer. Column chromatography is performed with silica gel (200-300 mesh).

Typical Procedure of Synthesis

Under the protection of argon, $[Ir(COD)Cl]_2$ (5.1 mg, 0.0075 mmol), (rac)-BINAP (12.1 mg, 0.0195 mmol) and 1.0 mL 1,2-dichloroethane are added to a Schlenk tube. The solution obtained is stirred at room temperature. 30 minutes later, oxanorbornadiene (63 mg, 0.3 mmol) and another 1.0 mL 1,2-dichloroethane are added, and the stirring is continued for additional 20 minutes. After the addition of 4-Ethynylanisole (55.5 mg, 0.42 mmol), the Schlenk tube is sealed with a rubber septum and moved to an oil bath. The mixture is stirred at 70° C. (bath temperature) until the reaction is complete. After vacuum evaporation of the reaction solvent, the residue is purified by column chromatography on silica and yellow oil is obtained as product (61.6 mg, 60% yield).

27A (1): Yellow oil, 60% yield. $^1$H NMR (400 MHz, $CDCl_3$): δ 7.32-7.25 (m, 2H), 6.78-6.70 (m, 2H), 5.29 (dd, J=4.84, 1.01 Hz, 1H), 5.23 (d, J=1.02 Hz, 1H), 3.77 (s, 3H), 3.75 (s, 3H), 3.72 (s, 3H), 2.78 (dd, J=8.45, 4.07 Hz, 1H), 2.12-2.05 (m, 1H), 1.99-1.93 (m, 1H). $^{13}$C NMR ($CDCl_3$, 100 MHz): δ 161.6, 161.5, 158.4, 132.0, 114.3, 112.8, 87.7, 84.9, 80.4, 79.8, 51.2, 51.4, 33.1, 29.3. HRMS (ESI) calcd for $C_{19}H_{18}O_6$ $[M]^+$: 342.1103. Found: 342.1098.

27B (2): Yellow oil, 59% yield. $^1$H NMR (400 MHz, $CDCl_3$): δ 7.37-7.32 (m, 2H), 6.83-6.78 (m, 2H), 5.35 (dd, J=4.81, 1.02 Hz, 1H), 5.30 (d, J=1.04 Hz, 1H), 4.32-4.24 (m, 4H), 3.80 (s, 3H), 2.86 (dd, J=8.32, 4.05 Hz, 1H), 2.19-2.12 (m, 1H), 2.08-2.01 (m, 1H), 1.36-1.30 (m, 6H). $^{13}$C NMR ($CDCl_3$, 100 MHz): δ 163.1, 162.4, 162.3, 159.4, 152.7, 144.2, 143.2, 142.7, 133.1, 115.4, 113.8, 88.9, 86.0, 85.1, 81.3, 80.8, 61.5, 61.4, 55.2, 34.3, 30.4, 14.1. HRMS (ESI) calcd for $C_{21}H_{22}O_6$ $[M]^+$: 370.1416. Found: 370.1420.

FCL-1-17 (3): Yellow oil, 55% yield. $^1$H NMR (400 MHz, $CDCl_3$): δ 7.37-7.32 (m, 2H), 6.83-6.78 (m, 2H), 5.26 (d, J=4.52 Hz, 1H), 5.21 (d, J=1.03 Hz, 1H), 3.80 (s, 3H), 2.84 (dd, J=8.32, 4.05 Hz, 1H), 2.15-2.08 (m, 1H), 2.06-1.99 (m, 1H), 1.52 (s, 9H), 1.51 (s, 9H); $^{13}$C NMR ($CDCl_3$, 100 MHz): δ 161.7, 161.5, 159.3, 144.3, 142.8, 133.1, 115.5, 113.8, 89.3, 86.0, 82.7, 82.6, 81.1, 80.9, 55.3, 34.4, 30.4, 28.1. HRMS (ESI) calcd for $C_{25}H_{30}O_6$ [M]$^+$: 426.2042. Found: 426.2038.

Cytotoxicity Assay

In this study, the compounds 1, 2 and 3 are dissolved in dimethyl sulfoxide (DMSO) to make stock solutions and further diluted in culture medium for this experiment, while cantharidin is used as positive control. Human cancer cell lines, including two breast adenocarcinoma cell lines (MCF-7 and MDA-MB-231), one gastric adenocarcinoma cell line (MKN-45), one colon carcinoma cell line (DLD-1), one oesophageal carcinoma cell line (KYSE-150) and one hepatocellular carcinoma cell line (HepG2) are cultured in RPMI 1640 or DMEM medium, containing 10% fetal bovine serum and 1% antibiotics (Penicillin and strep). The cell lines are cultured at 37° C. in a humidified environment containing 5% $CO_2$. To determine the effects of the compounds on cell viability, a standard colorimetric 3-(4,5-dimethylthiazol-2-yl)-2, 5-diphenyltetrazolium bromide (MTT) assay is used to test the viable cell number. Cells are seeded in a 96-well plate ($4 \times 10^3$ cells/well) and allowed to attach overnight.

After the recovery, cells are treated with 1.56 µM, 3.125 µM, 6.25 µM, 12.5 µM, 25 µM, 50 µM of each of the compounds in culture medium for 48 hrs. Then, 20 µL of MTT (5 mg/mL stock in PBS) per well is added into the medium (200 µL) and incubated for 4 hrs at 37° C. Finally, the culture medium is removed and 200 µL of DMSO are added to each well to dissolve the purple formazan crystals. Absorbance of the solution is measured using microplate reader spectrophotometer (Bio-Rad Laboratories, Inc., Hercules, Calif.) at a wavelength of 570 nm.

Wound Healing Assay

A wound healing assay is performed as follows: KYESE-150 cells are seeded in each well of the 12-well plate at 50% confluence in completed medium. After 24 hrs seeding, the monolayer is wounded by scoring with a sterile plastic tip (1 mL), then washed several times with medium to remove cell debris and then incubated in conditioned medium in the absence or presence of the tested compounds for various periods of time up to 72 h. The concentration which does not alter the viability of KYESE-150 cells are chosen (1 µM/mL and 2.5 µM/mL). Cell migration into the wound surface is monitored by Olympus IX71 microscopy and digitally photographed.

INDUSTRIAL APPLICABILITY

The chemical entities of the present invention are useful for therapeutic purposes due to their anti-cancer and anti-migration activities. The synthesis method of the chemical entities of the present invention is also useful for preparing a pharmaceutical composition comprising the chemical entities originated from natural sources and further synthesized to become an effective agent for treating and/or preventing various cancers.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What is claimed is:

1. A composition comprising norcantharidin analogues represented by a general formula of (I):

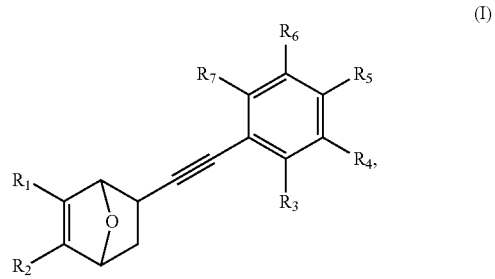

wherein $R_1$ and $R_2$ are independently or jointly selected from hydrogen, halogen, alkyl, alkenyl, alkynyl, hydroxyl, alkoxyl, amine, nitro, alkylthio, or heteroalkyl; and wherein $R_3$, $R_4$, $R_5$, $R_6$, and $R_7$ are independently or jointly selected from hydrogen, halogen, alkyl, alkenyl, alkynyl, hydroxyl, alkoxyl, amine, nitro, nitrile, alkylthio, trifluoromethyl, alkyl sulfonyl, or aryl sulfonyl.

2. The composition of claim 1, wherein said norcantharidin analogues further comprise at least one of the following structures:

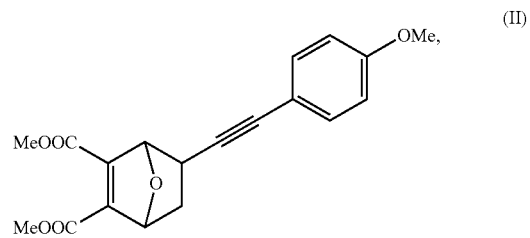

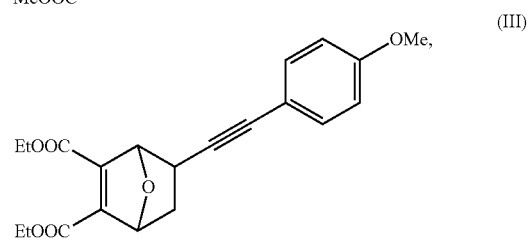

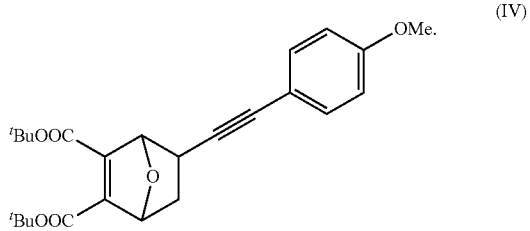

3. The composition of claim 1, wherein oxanorbornadiene derivatives are first isolated from a natural source or obtained from a chemically synthesized compound, followed by reacting said oxanorbornadiene derivatives with a chemical ligand under a transition metal-catalyzed alkynylation reaction in the presence of a solvent in order to result in said norcantharidin analogues.

4. The composition of claim 3, wherein a transition metal used in said transition metal-catalyzed alkynylation reaction is an iridium-based compound.

5. The composition of claim 4, wherein said iridium-based compound comprises Ir(I)(COD)Cl, [Ir(I)(COD)Cl]$_2$, Ir(I)(COD)(acac) and Ir(III)(C$_7$H$_8$)$_3$(acac).

6. The composition of claim 3, wherein said solvent comprises 1,2-dichloroethane, tetrahydrofuran, dimethoxyethane, toluene, EtOAc and i-PrOH.

7. The composition of claim 3, wherein said chemical ligand is 4-Ethynylanisole.

8. The composition of claim 1 is administered to a subject in need thereof in order to inhibit growth of cancer cells or tumor cells in said subject, said cancer cells or tumor cells comprising hepatoma, breast, oesophageal, colorectal and lung carcinoma cells.

9. A method of synthesizing norcantharidin analogues for preparing a medicament for inhibiting growth of cancer or tumor cells, said method comprising:

isolating oxanorbornadiene derivatives from a natural source or obtaining said derivatives from a chemically synthesized compound; and reacting said oxanorbornadiene derivatives with a chemical ligand under a transition metal-catalyzed alkynylation in the presence of a solvent, said norcantharidin analogues being represented by a general formula of (I):

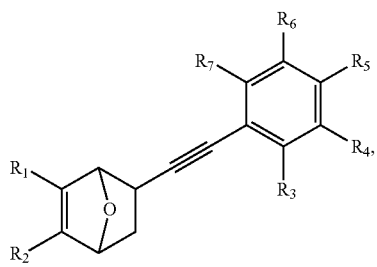

(I)

wherein R$_1$ and R$_2$ are independently or jointly selected from hydrogen, halogen, alkyl, alkenyl, alkynyl, hydroxyl, alkoxyl, amine, nitro, alkylthio, or heteroalkyl; and wherein R$_3$, R$_4$, R$_5$, R$_6$, and R$_7$ are independently or jointly selected from hydrogen, halogen, alkyl, alkenyl, alkynyl, hydroxyl, alkoxyl, amine, nitro, nitrile, alkylthio, trifluoromethyl, alkyl sulfonyl, or aryl sulfonyl.

10. The method of claim 9, wherein said transition metal-catalyzed alkynylation comprising using an iridium-based catalyst.

11. The method of claim 10, wherein said iridium-based catalyst comprises Ir(I)(COD)Cl, [Ir(I)(COD)Cl]$_2$, IR(I)(COD)(acac) and Ir(III)(C$_7$H$_8$)$_3$(acac).

12. The method of claim 9, wherein said chemical ligand is 4-Ethynylanisole.

13. The method of claim 9, wherein said solvent comprises 1,2-dichloroethane, tetrahydrofuran, dimethoxyethane, toluene, EtOAc and i-PrOH.

14. The method of claim 9, wherein said norcantharidin analogues further comprises at least one of the following structures:

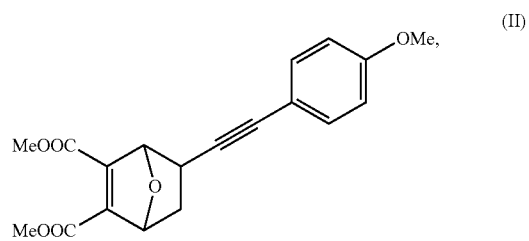

(II)

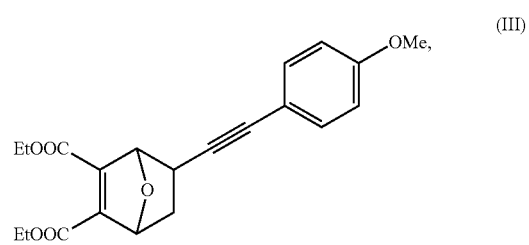

(III)

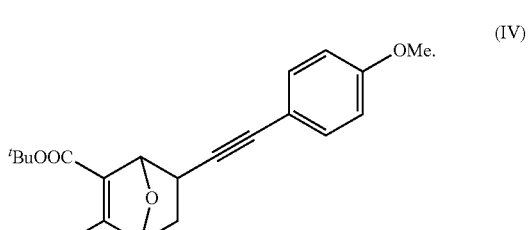

(IV)

15. A method for inhibiting growth of cancer cells or tumor cells comprising administering a composition containing an effective amount of norcantharidin analogues to a subject in need thereof, said cancer cells or tumor cells comprising hepatoma, breast, oesophageal, colorectal and lung carcinoma cells, said norcantharidin analogues having a general formula of (I):

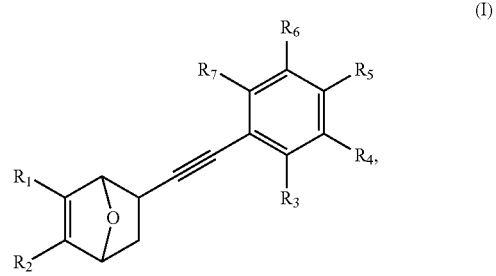

(I)

wherein R$_1$ and R$_2$ are independently or jointly selected from hydrogen, halogen, alkyl, alkenyl, alkynyl, hydroxyl, alkoxyl, amine, nitro, alkylthio, or heteroalkyl; and wherein R$_3$, R$_4$, R$_5$, R$_6$, and R$_7$ are independently or jointly selected from hydrogen, halogen, alkyl, alkenyl, alkynyl, hydroxyl, alkoxyl, amine, nitro, nitrile, alkylthio, trifluoromethyl, alkyl sulfonyl, or aryl sulfonyl.

16. The method of claim 15, wherein said norcantharidin analogues further comprises at least one of the following structures:

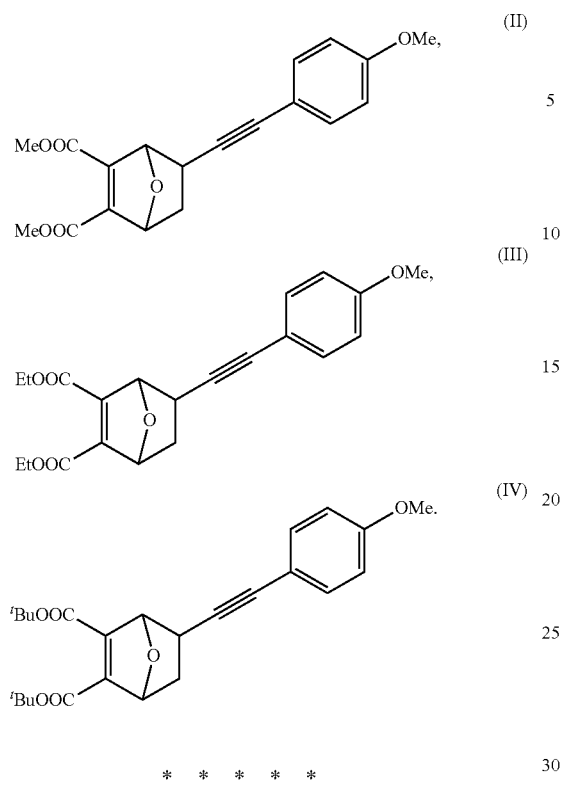
* * * * *